United States Patent [19]

Smulson et al.

[11] Patent Number: 5,272,057

[45] Date of Patent: Dec. 21, 1993

[54] METHOD OF DETECTING A PREDISPOSITION TO CANCER BY THE USE OF RESTRICTION FRAGMENT LENGTH POLYMORPHISM OF THE GENE FOR HUMAN POLY (ADP-RIBOSE) POLYMERASE

[75] Inventors: Mark E. Smulson, Washington, D.C.; Kishor Bhatia, Arbutus, Md.; Konrad Huppi, Reston, Va.

[73] Assignee: Georgetown University, Washington, D.C.

[21] Appl. No.: 257,696

[22] Filed: Oct. 14, 1988

[51] Int. Cl.$^5$ .................. C12Q 1/68; C07H 21/04
[52] U.S. Cl. ........................ 435/6; 536/24.31; 536/24.3; 935/77; 935/78
[58] Field of Search ............. 435/6; 436/501; 536/28; 935/77, 78

[56] References Cited

FOREIGN PATENT DOCUMENTS 0229674 7/1987 European Pat. Off. ............. 435/6

OTHER PUBLICATIONS

SenGupta et al., Biochem. Biophys. Commun. 136(1):341–347 (Apr. 14, 1986).
Lidgreau et al., PNAS (USA) 82:7068–7070 (1985).
Alkhatib et al., PNAS (USA) 84:1224–1228 (1987).
Olszewska et al., Oncogene 1(4):403–408 (1987) Biol. Abstr. 85(4):38841.
Paulsen et al., Tiss. Antigns 29(4):186–194 (1987) Biol. Abstr. 84(8):76620.
Kato et al., Leukemia 2(10):701–703 (1988) Biol. Abstr. 87(1):6774.
Clifford et al., Biochem. Soc. Trans. 17(2):408 (1989) (Abstr) DBA Acc. #89-13642 (Dialog).
Bhatia et al., Cancer Res. 50:5406–5413 (1990).
Kasid, U. N. et al., *Carcinogenesis* 7:327–330 (1986).
Miwa, M. et al., *Arch. Biochem. Biophys.* 181:313–321 (1977).
Burzio, L. et al., *Proc. Soc. Exp. Biol. Med.* 149:933–938 (1975).
Hirai, K. et al., *Cancer Research* 43:3441–3446 (1983).
Harris, A. L., *Int. J. Radiat. Biol.* 48:675–690 (1985).
Smulson and Sugimura, "Novel ADP-Ribosylations of Regulatory Enzymes and Proteins," *Developments in Cell Biology*, vol. 6, Eslevier, (1980).
Benjamin and Gill, *J. Biol. Chem.* 255:10502–10508 (1980).
Alkhatib, H. M. et al., *Proc. Natl. Acad. Sci. USA* 84:1224–1228 (1987).
Kurosaki, T. et al., *J. Biol. Chem.* 262:15990–15997 (1987).
Cherney, B. W. et al., *Proc. Natl. Acad. Sci. USA* 84:8370–8374 (1987).

Primary Examiner—Margaret Moskowitz
Assistant Examiner—Stephanie W. Zitomer
Attorney, Agent, or Firm—Sterne, Kessler, Goldstein & Fox

[57] ABSTRACT

The invention relates to a method for detecting the presence of a DNA polymorphism associated with predisposition for certain cancers in a human. This method involves analyzing the human chromosome 13 using a hybridization probe which will hybridize to the gene for human poly (ADP-ribose) polymerase wherein the probe is capable of identifying the DNA polymorphism.

20 Claims, No Drawings

METHOD OF DETECTING A PREDISPOSITION TO CANCER BY THE USE OF RESTRICTION FRAGMENT LENGTH POLYMORPHISM OF THE GENE FOR HUMAN POLY (ADP-RIBOSE) POLYMERASE

BACKGROUND OF THE INVENTION

Part of the work leading to this invention was made with U.S. Government funds. The U.S. Government has certain rights in this invention.

1. Field of the Invention

This invention relates to a method of detecting a predisposition for cancer using restriction fragment length polymorphism with a human poly (ADP-ribose) polymerase hybridization probe.

2. Brief Description of the Background Art

Carcinogenesis is a multistep process initiated by DNA damage, gene mutation, gene rearrangement and gene translocation, and ending with phenotypic transformation of cancer cells. Bishop, *Science* 235:305-311 (January 1987).

It is well documented that normal cellular genes ("proto-oncogenes") can be converted into oncogenes or cancer genes due to agents which cause DNA strand breaks and damage. Kasid, U.N. et al. *Carcinogenesis,* 7:327-330 (1986). Often, conversion involves the breakage of the proto-oncogene from DNA and its movement and placement through another break into another chromosome. Also, it is known that proto-oncogenes can become activated to become malignant oncogenes by gene amplification. Stark and Wahl, *Ann. Rev. Biochem.* 53:447-491 (1984).

Most living cells possess systems for recognizing and eliminating DNA damage. For example, the prokaryote, *E. coli,* possesses a variety of enzymes for responding to DNA damage. Such enzymes include those of the SOS repair system and various Rec proteins. These enzymes, and others, respond to DNA damage caused by U.V. radiation, chemical mutagens and the like. Eukaryotic and mammalian cells also possess DNA repair enzymes.

One mammalian enzyme, poly (ADP-ribose) polymerase, appears to play an important role in recovery of cells from DNA strand-breaking events. It has been reported that poly (ADP-ribose)polymerase activity is higher in isolated nuclei of SV 40 transformed fibroblasts than in those of untransformed fibroblasts; that leukemic cells showed higher enzyme activity than normal leukocytes; and that colon cancers showed higher enzyme activity than normal colon mucosa. Miwa et al., *Arch. Biochem. Biophys.* 181:313-321 (1977); Burzio et al., *Proc. Soc. Exp. Biol. Med.* 149:933-938 (1975); Hirai et al., *Cancer Res.* 43:3441-3446 (1983). It was concluded in these reports that the activity of the poly (ADP-ribose) polymerase responds to DNA damage and parallels DNA repair. It has also been reported that the reduction of activity of poly (ADP-ribose) polymerase by drugs increases DNA amplification and consequent oncogenesis in cells. Harris, *Int. J. Radiat. Biol.* 48:675-690 (1985).

In recent years, much work has centered around the exact mechanism by which poly(ADP-ribose)polymerase modulates the DNA replication/repair processes of mammalian cells. Smulson and Sugimura, eds., "Novel ADP-Ribosylations of Regulatory Enzymes and Proteins," Elsevier, N.Y. (1980). It is known that this enzyme is a 113 kDa protein which uses NAD as a substrate in the formation of poly (ADP-ribose) polymerase chains at sites on many nuclear proteins. The enzyme binds tightly to DNA and requires DNA strand breaks for enzymatic activity. Benjamin and Gill, *J. Biol. Chem.* 255:10502-10508 (1980). It has been hypothesized that the enzyme system functions in response to transient and localized DNA strand breaks in cells that may arise through a variety of processes including DNA repair, replication, recombination and gene rearrangement. Alkhatib et al., *PNAS USA* 84:1224-1228 (1987). One reference has taught the measuring of the activity of this enzyme as a method of detecting a predisposition to cancer. Pero, European Patent No. 229,674, published Jul. 22, 1987.

In order to more precisely define the role of poly (ADP-ribose) polymerase, the gene for this enzyme has been sequenced and cloned and localized.

For instance, Kurosaki et al., *J. Biol. Chem.* 262:15590 (Nov. 25, 1987) describes the sequence of cDNA clones representing most of a 4.9 kb mRNA for human poly (ADP-ribose) synthetase from transformed human fibroblasts. The investigators showed the restriction endonuclease map for the cloned cDNAs which reveals two HindIII sites and one PstI site.

In Cherney et al., *Proc. Natl. Acad. Sci. (USA)* 84:8370 (December 1987), two of the present inventors and co-authors disclose the first intact cloned CDNA sequence of human poly (ADP-ribose) polymerase. They also disclosed the restriction endonuclease map with two PstI sites and two HindIII sites. RLFP analysis was done on normal individuals' lymphocytes and fibroblast cell lines to determine chromosome location and two HindIII allele polymorphism were observed on chromosomes in samples from normal patients. It was concluded that the active and expressed gene was on human chromosome one and the processed pseudogene was on chromosome 13.

Thus, the recent cloning of the cDNA for the nuclear enzyme poly (ADP-ribose) polymerase allowed for subsequent detailed sequence analysis of this nuclear protein as well as detailed human chromosomal localization and initial characterizations of the polymorphism of this gene in the normal human population.

The present invention is based on the unexpected finding that the polymorphism detected by cDNA for poly (ADP-ribose) polymerase is linked to a predisposition for cancer.

SUMMARY OF THE INVENTION

The invention relates to a method for detecting the presence of a DNA polymorphism associated with susceptibility for cancer in a human. This method involves analyzing the human chromosome 13 using a hybridization probe which will hybridize to the gene for human poly (ADP-ribose) polymerase wherein the probe is capable of identifying the DNA polymorphism.

DETAILED DESCRIPTION OF THE INVENTION

At its broadest, the invention comprises a method of detecting the presence of a DNA polymorphism associated with susceptibility to cancer in a human by analyzing the human chromosome 13 using a hybridization probe containing nucleotide sequence information for poly (ADP-ribose) polymerase capable of identifying the DNA polymorphism.

The use of restriction fragment length polymorphism (RFLP) is only one preferred embodiment of detecting polymorphism. Since, ultimately, the use of RFLP depends on polymorphism in DNA restriction sites along the nucleic acid molecule, other methods of detecting the polymorphism can also be used. Any method of analysis which yields the linkage between the polymorphism that can be detected by the poly (ADP-ribose) polymerase hybridization probe or a probe of the exact polymerase sequence or adjacent sequence found on chromosome 13 and a predisposition to cancer can be utilized. Techniques such as direct location of the polymorphism on chromosome 13 by radiolabelling, fluorescent labelling or enzyme labelling may be utilized. Other suitable techniques include polymerase chain reaction, ribonuclease mis-match cleavage assay and direct oligonucleotide hybridization.

However, the most preferred method for carrying out the present invention involves RFLP techniques. The following related definitions are provided to assure uniformity and to avoid ambiguity.

Poly (ADP-ribose)polymerase. A chromatic associated enzyme which is a 113 kDa protein that uses NAD as a substrate to catalyze both the covalent transfer of ADP-ribose to a variety of nuclear protein acceptors and subsequently catalyzes the transfer of an additional 60–80 ADP-ribose units to the initial moiety.

Deoxyribonucleic Acid (DNA). DNA is the molecular basis of heredity. DNA consists of a polysugar-phosphate backbone from which the purines and pyrimidines project. The backbone is formed by bonds between the phosphate molecule and carbon 3 and carbon 5 of adjacent deoxyribose molecules. The nitrogenous base extends from carbon 1 of each sugar. According to the Watson-Crick model, DNA forms a double helix that is held together by hydrogen bonds between specific pairs of bases (thymine to adenine and cytosine to guanine). Each strand in the double helix is complementary to its partner strand in terms of its base sequence.

Restriction Endonuclease. A restriction endonuclease (also restriction enzyme) is an enzyme that has the capacity to recognize a specific base sequence (usually 4, 5, or 6 base pairs in length) in a double-stranded DNA molecule, and to cleave both strands of the DNA molecule at every place where this sequence appears. For example, EcoRI recognizes the base sequence GAATTC/CTTAAG.

Restriction Fragment. The DNA molecules produced by digestion with a restriction endonuclease are referred to as restriction fragments. Any given genome will be digested by a particular restriction endonuclease into a discrete set of restriction fragments.

Restriction Fragment Length Polymorphism (RFLP). The genomic DNA of two individuals in a population will differ in sequence at many sites either as a result of change in bases or insertions or deletions of sequences. When these differences occur in the recognition site for a restriction endonuclease, then a polymorphism in the length of restriction fragments produced by digestion of the DNA of the two individuals will result. For example, the hypothetical pattern of restriction fragments produced by digestion of A and B with restriction enzyme EcoRI exhibits a polymorphism, since the DNA of individual A yields two fragments f and g of lengths 1,600 base pairs and 2,400 base pairs, while DNA of individual B does not yield EcoRI fragments of this size after digestion with EcoRI, but instead gives a single fragment h of length 4,000 base pairs. As used herein, a polymorphism is also referred to as a "pattern."

Agarose Gel Electrophoresis. To detect a polymorphism in the length of restriction fragments, an analytical method for fractioning double-stranded DNA molecules on the basis of size is required. The most commonly used technique (though not the only one) for achieving such a fractionation is agarose gel electrophoresis. The principle of this method is that DNA molecules migrate through the gel as though it were a sieve that retards the movement of the largest molecules to the greatest extent and the movement of the smallest molecules to the least extent. Note that the smaller the DNA fragment, the greater the mobility under electrophoresis in the agarose gel.

The DNA fragments fractionated by agarose gel electrophoresis can be visualized directly by a staining procedure if the number of fragments included in the pattern is small. The DNA fragments of genomes can be visualized successfully. However, most genomes, including the human genome, contain far too many DNA sequences to produce a simple pattern of restriction fragments. For example, the human genome is digested into approximately 1,000,000 different DNA fragments by EcoRI. In order to visualize a small subset of these fragments, a methodology referred to as the Southern hybridization procedure can be applied.

Southern Transfer Procedure. The purpose of the Southern transfer procedure (also referred to as blotting) is to physically transfer DNA fractionated by agarose gel electrophoresis onto a nitrocellulose filter paper or another appropriate surface or method, while retaining the relative positions of DNA fragments resulting from the fractionation procedure. The methodology used to accomplish the transfer from agarose gel to nitrocellulose is to draw the DNA from the gel into the nitrocellulose paper by capillary action.

Nucleic Acid Hybridization. Nucleic acid hybridization is a technique which has been used in a wide variety of contexts in molecular biology since the basic principles governing reassociation of complementary nucleic acid molecules were discovered during the 1960s. Nucleic acid hybridization depends on the principle that two single-stranded nucleic acid molecules that have complementary base sequences will reform the thermodynamically favored double-stranded structure if they are mixed in solution under the proper conditions. The double-stranded structure will be formed between two complementary single-stranded nucleic acids even if one is immobilized on a nitrocellulose filter. In the Southern hybridization procedure, the latter situation occurs. As noted previously, the DNA of the individual to be tested is digested with a restriction endonuclease, fractionated by agarose gel electrophoresis, converted to the single-stranded form, and transferred to nitrocellulose paper, making it available for reannealing to the hybridization probe.

Hybridization Probe. To visualize a particular DNA sequence in the Southern hybridization procedure, a labelled DNA molecule or hybridization probe is reacted to the fractionated DNA bound to the nitrocellulose filter. The areas on the filter that carry DNA sequences complementary to the labelled DNA probe become labelled themselves as a consequence of the reannealing reaction. The areas of the filter that exhibit such labelling are visualized. The hybridization probe is generally produced by molecular cloning of a specific DNA sequence from the human genome.

In the method according to this invention, a biological sample having nucleated cells is obtained from a human. The nucleated cells are then isolated according to means known in the art, with the subsequent step involving isolation of the DNA from the nucleated cells, again using means known in the art.

The isolated DNA is then digested with a restriction enzyme, selected from one of the following enzymes: HindIII, Pst1, or EcoR1. The DNA fragments are then separated according to their molecular weights to form a pattern, typically using electrophoresis. The DNA polymorphism associated with a predisposition for cancer, if present, can be detected using a hybridization probe which will hybridize to the gene for human poly (ADP-ribose) polymerase wherein the probe will also hybridize to a DNA fragment in a human with a predisposition for cancer.

Each restriction enzyme presents its own restriction fragment length pattern or polymorphism. In those humans with a predisposition for cancer, DNA digests with HindIII show two patterns: an "ab" pattern (2.6±0.1 kb and 2.9±0.2 kb) and a "b" pattern (2.6±0.1 kb). Normal humans show a HindIII restriction fragment pattern of about 2.9±0.1 kb. See FIG. 1.

DNA digests with Pst1 show a polymorphism of about 5.7 to about 6.1 kilobases in those humans with predispositions for cancer. Normal humans show a restriction fragment of about 7 to about 7.5 kilobases in Pst1 digests.

DNA digests with EcoR1 show a polymorphism of about 5.1 in those humans with a predisposition for cancer. Normal humans show a restriction fragment of about 5.3 in EcoR1 digests.

As used herein, the term "normal" means those individuals that do not display any cancerous or precancerous conditions, measured by clinical, symptomatic or morphological means.

In one embodiment of this invention, the progression of a tumor's pathogeneity in tumor biopsy samples can be followed. By examining the changes in the polymorphic bands in patients with cancer, this method can be used for monitoring tumor therapy in diseases such as metastatic cancer, solid tumors, and AID's related lymphomas. Thus, the probe can be used in the method of this invention to establish the polymorphisms in the tumor sample. After treatment for cancer, by chemotherapy or radiotherapy, the biopsy tumor sample can again be assayed for the presence of the polymorphisms. Using the HindIII restriction enzyme, for example, it has been determined that in cancer patients who have an ab pattern before treatment (with bands showing at 2.6 and 2.9 kb), there is a loss of the 2.9 kb (a) band after treatment, with a concomitant reduction in the pathogenicity of the tumor.

The size of the DNA fragments are given in ranges because it is well known that due to the nature of the techniques used in determining fragment size, small differences in measurements results are not uncommon. These differences do not, however, detract from the accuracy of the numbers given.

As used herein, the term "humans with a predisposition or with a susceptibility for cancer" is meant to include individuals that may not yet show or display any cancerous or precancerous conditions, as measured by symptomatic means, but may be inclined to develop cancer. As detailed in the data in the Examples, all cancer patients tested showed the polymorphisms or patterns when tested according to the method of this invention, individuals that did not have cancer or precancerous conditions did not show these polymorphisms or patterns. A small group of individuals that did not have cancer or precancerous conditions did show the polymorphisms or patterns. These individuals, or others who also show these patterns, need to be followed to determine if individuals subsequently show precancerous or cancer cells.

The types of cancers for which a predisposition may be detected by the methods of the invention include, but are not limited to, Burkitt's lymphoma, B follicular cell lymphoma, small cell lung carcinoma, colon-rectal carcinoma and breast adenocarcinoma.

Suitable biological samples having nucleated cells that may be used in this invention include, but are not limited to, blood, semen and tissue. The method of obtaining the biological sample will vary depending upon the nature of the sample.

By the term "nucleated cells" is meant any cell containing a nucleus. Examples of such cells include, but are not limited to, white blood cells, epithelial cells, sperm cells, or mesenchymal cells. Such cells may either be normal or neoplastic.

DNA from the nucleated cells is isolated, using any of the techniques known to those skilled in the art of the invention. For instance, DNA can be isolated using various lytic enzymes or chemical solutions and centrifugation. Blin and Stafford, *Nucl. Acid Res.* 3:2303–2308 (1976). DNA may also be isolated using size exclusion chromatography.

After the DNA is isolated from the cells' nuclei, it is digested with a given restriction endonuclease. The restriction endonucleases that may be used in this invention are HindIII, PstI, or EcoRI. Given the ability of the poly (ADP-ribose) polymerase hybridization probe to detect polymorphism on Chromosome 13, it is possible that other RFLPs may be detected using other restriction enzymes. For example, these restriction enzymes may include MSP 1, Not 1, Clo 1, or any other appropriate enzymes.

After a digest is obtained, and the same is separated by standard technique, such as, for example, agarose gel electrophoresis, the separated bands are probed with a DNA fragment encoding poly (ADP-ribose) polymerase. The preferred probe of the invention is cDNA encoding human poly (ADP-ribose)polymerase, although genomic DNA or mRNA may al so be used as the probe. Further, any probe may be used which detects sequences linked or associated with poly (ADP-ribose) polymerase on chromosome 13. The cDNA sequence of the preferred probe has been described in Cherney, et al. PNAS(USA), 84: 8370-8374 (1987), herein incorporated by reference. In addition, the probes may hybridize to a portion of fragment of the gene for poly (ADP-ribose) polymerase or genes or sequences linked or associated with poly (ADP-ribose) polymerase.

Preferably, more than one polymorphism is utilized for the detection of predisposition for cancer. Thus, DNA from the biological sample can be subjected to three separate restriction enzyme digests using HindIII, Pst1, and EcoR1. It is to be understood that three digests are conducted on three DNA samples, although from the same biological source.

The hybridization probe of this invention may be labelled by standard labelling techniques such as with a radiolabel, enzyme label, fluorescent label, biotin-avidin label, chemiluminescence, and the like, and, after hybridization, are detected. Comparison of the RFLP or RFLP's for the subject under investigation will quickly reveal the presence or absence of the polymorphism linked to predisposition to cancer.

The materials for use in the invention are ideally suited for the preparation of a kit. Such a kit may comprise a carrier means being compartmentalized to receive in close confinement one or more container means such as vials, tubes and the like, each of said container means comprising one of the separate elements to be used in the method.

For example, a first container may contain a hybridization probe. The second container may contain the restriction enzyme to be used in the digest. Other containers may contain reagents useful in the localization of labelled probes, such as enzyme substrates. Still other containers may contain buffers, etc.

Having now generally described the invention, the same will be understood by means of specific examples which are, however, not intended to be limiting unless otherwise specified.

EXAMPLE 1

1. Introduction

Burkitt's lymphoma is a neoplasm of B lymphocytes. Two subtypes of this disease have been described, endemic and sporadic, which differ at clinical and biological levels. Klein, George, *Cellular Oncogene Activation*, Marcel Dekker, Inc. (1988). Both forms are associated with consistent chromosomal translocations that place the c-myc proto-oncogene, a gene associated with cell proliferation, within or in proximity to an immunoglobulin chain gene locus.

The mouse plasmacytoma system offers the closest analogy to the human Burkitt's tumor. Thus, mouse plasmacytomas (MOPC) are B cell neoplasms, and like Burkitt's lymphoma, are closely associated with a translocation that places the myc proto-oncogene under the putative control of an immunoglobulin locus. Furthermore, it has been suggested that the anatomical involvement of the jaw in endemic Burkitt's may be related to a prerequisite inflammatory condition, similar to the obligate requirement of pristane in induction of plasmacytomas in susceptible strains.

2. Human Studies

Observations from MOPC studies prompted studies to determine whether structural differences in the polymerase gene(s) would be present in the human analog of the MOPC system. Initially, the possible genotypes for the polymerase gene(s) from human DNA were defined. When human genomic DNA from several sources was digested with HindIII, three main patterns were distinguishable:
(1) a single band present at 2.8 kb (genotype ab);
(2) two bands present in that region at 2.8 and 2.6 kb (haploid ab); or
(3) a single band present at 2.6 kb (genotype b).

Based on hamster and human somatic cell hybrids, it had been previously shown that these bands arise from chromosome 13. When the same DNA samples were analyzed after digesting them with Pst1, a band of 5.6 kb in all samples that had an ab genotype. was observed. In samples with a "b" genotype it could be deduced that this band arose from a 7 kb Pst1 band. This suggested that the polymorphism in the HindIII 2.8 kb band probably arose as a result of deletion involving a Pst1 site flanking the polymerase gene on chromosome 13.

To confirm this finding, the same genomic DNA was digested with EcoRI. Since it had been earlier shown that the 5.3 kb band in the Southern digests of total genomic DNA represents polymerase sequences on chromosome 13, a deletion event in this region to yield a lower hybridizing band was expected. It was found that DNA samples representing genotypes ab or b resulted in an EcoR1 band of slightly greater mobility than the 5.3 kb band in genotype a, typically a 5.1 kb band.

To further analyze the frequency of these genotypes in a control population, DNA from 94 non-cancer individuals was screened. As described in Table 1, genotype a was found to be the most predominant form in this sample population. Thirteen of the 94 individuals showed an ab genotype. In the total normal cell population screened, no individuals with a b genotype could be found. Since both the 2.8 kb and the 2.6 kb HindIII bands are allelomorphic, one would expect, based on Mendelian inheritance, to find a subpopulation for the b genotype. Thus, it is thought that based on the Hardy Weinberg principle, the b genotype would be of a low frequency.

3. Human Studies of DNA from Burkitt's Lymphoma.

DNA from 45 Burkitt's lymphoma was also studied. These included both cell lines and primary tumor samples. This sample size was comprised of 20 samples from endemic Burkitt's lymphomas and 23 from sporadic Burkitt's lymphomas. The samples were digested with HindIII.

The results showed that the total frequency of an ab or b genotype in these samples was significantly greater than in control samples. Thus approximately 70% of total Burkitt's lymphoma DNA was polymorphic for the rarer genotypes. In endemic Burkitt's, the frequency of this pattern approached 100% (19/20), a high proportion of which were of b genotypes (42%) 19/20. In sporadic Burkitt's the frequency of ab or a "b" genotype was significantly greater than in normal, non-cancer individuals (11 out of 23 cases compared to 14 out of 94 normal cases).

In sporadic Burkitt's, we also found that the presence of ab or b genotype cosegregated with the EBV status. Thus, almost 100% of the polymorphic samples from sporadic Burkitt's were EBV. In fact, the only EBV-+sample was from a patient who was a native of Africa, but developed BL several years after living in the USA. Since almost all samples from endemic Burkitt's showed genotype b or ab and since endemic Burkitt's is almost always associated with EBV, the presence of this genotype appears to reflect an independent factor involved with the induction of Burkitt's lymphoma. The results on these studies are summarized in Table 2.

The presence of increase frequency of an altered polymerase gene in Burkitt's lymphoma corroborates the observations of Potter, M. et al. (Genomics 2:157–262 (1988) that certain Burkitt's cell lines are deficient in DNA repair following X-irradiation, similar to the observations with cells from the plasmacytoma susceptible and resistant mouse strains. A constraint to the key involvement of the polymerase and DNA repair deficiency in both Burkitt's and plasmacytoma formation is the selectivity of the transformed target cell. Thus, in contrast to other DNA deficient conditions, for example Fanconi's anemia and Blooms syndrome that predispose towards development of a wide variety of tumors, one would have to hypothesize a selective mode of polymerase involvement in B cells.

4. Human Studies on Hematological Malignancies

It has recently been suggested that a number of hematological malignancies could arise as a result of aberrant recombination mediated by the immunoglobulin recombinase. A common factor for such malignancies is the juxtaposition of a proto-oncogene to an Ig locus. It is possible that the polymerase plays a role in immunoglobulin recombinase systems and the isotype switching. Aberrant recombination events would be increased in frequency in presence of a defective polymerase gene and such individuals would be predisposed to the development of B cell neoplasia that results from translocations at the Ig loci.

To test this hypothesis DNA samples from B Follicular cell lymphomas, Acute/Chronic Myeloid leukemias ("AML/CML") and Small cell lung carcinomas ("SCLC") were analyzed using HindIII. Since B follicular lymphomas are associated with a translocation of a proto-oncogene in the Ig loci, we would expect to find increased frequency of ab or b genotypes in these samples. Conversely since AML/CML and SCLC's are non lymphoid tumors, we would expect a normal distribution of the genotypes.

An increased frequency of ab and b genotypes was indeed found in samples from B follicular lymphomas. Of 24 samples, 11 of 19 samples were found to show a translocation to have either an ab or a b genotype. The distribution of genotype distribution in B follicular lymphomas is summarized in Table 3. 10 samples of myeloid tumors were examined and no increase in the frequency of ab or b genotype distribution in these samples was found. However, in SCLC samples we again found a very high frequency of ab or b genotypes. Furthermore, in this sample population the presence of ab or b genotype cosegregated with the presence of amplified L-myc, so that 100% of the L-myc amplified cases had either an ab or a "b" genotype. We also found three out of four non-small cell lung tumors to be polymorphic as shown in Table 4.

It thus appeared that the increased frequency of the ab or b genotype did not correlate selectively with lymphoid malignancies. Since these genotype patterns are localized to chromosome 13 and it has been suggested that the sequences n o chromosome 13 may represent a pseudogene, it is possible that the deletion event on chromosome 13 as observed by using the polymerase CDNA is not functionally related to the polymerase, but that the polymerase sequences have provided a fortuitous linkage marker for a possible recessive gene involved in predisposition to certain types of tumors.

Indeed, when the different cell types (those with "a", "ab" or "b" genotype were examined) for changes in the enzymatic activity and or the protein content of the polymerase, no correlation with altered gene structure and enzymatic activity was found as observed both by activity gel analysis and NAD content of the cells or by immuno-quantitation. A number of Burkitt's cell lines that represented all the three genotypes in the sample population were analyzed by Northern analysis. The results did not indicate any obvious differences in transcripts for the polymerase in these cells.

Recently Harbour, J. W., et al. Science 241:353 (1988) described abnormalities in the structure and expression of another gene on chromosome 13, the Retinoblastoma gene, in various SCLC cell lines. These findings were compared to deletion events on chromosome 13 linked to the polymerase. As seen in Table 5, there is a strong association of the polymerase linkage marker in the various samples we analyzed.

Since there is evidence in certain tumors that the inactivation of both alleles of certain genes triggers tumorigenesis and since no single normal DNA sample with a b genotype has been observed, but in contrast frequently a "b" genotype in tumor DNA has been found, it has been concluded that such a genotype could arise in certain cases by a deletion event affecting an "ab" genotype. To test this hypothesis, matched tumor and lymphocyte DNA samples for genotype characterization were analyzed. In all samples with b genotypes, it was found that the corresponding lymphocyte DNA has an ab genotype. Thus, it is possible that the b genotypes observed in earlier tumor samples could have arisen by a similar mechanism.

In all our samples from the tumor tissues, 19 samples with a "b" genotype have been found. In an equal control sample size no "b" genotype was found.

5. Human Studies on Breast Adenocarcinoma

Since it has been suggested that Breast adenocarcinoma is associated both with a heritable factor and a putative recessive oncogene, screening was extended to breast adenocarcinomas. As seen Table 6, 23 of 55 samples were found to be polymorphic. Among the samples that were matched for tumor and lymphocyte DNA, of significant interest were four samples, a sample that showed a conversion of the a genotype to an ab genotype in the tumor cells, two others that showed a conversion of an ab genotype to a "b" genotype in the tumor cells. In one case, the tumor genotype was found to be an a but the somatic genotype to be an ab. However, in this case there appeared to be an amplification event suggesting that the a in the tumor probably arose of a chromosomal rearrangement. Thus, further supporting the earlier observation that the b genotype is tumor specific.

The linkage of Rb and poly(ADP-Ribose) polymerase has now been characterized on chromosome 13 and it is known that the polymerase is localized further down from the R6 on 13 q. It is situated close to the ter. In accordance with Knudson's ingenious hypothesis, it is proposed that this deletion even on chromosome 13 as observed by the cDNA to the poly(ADP-Ribose) polymerase, represents a part of the two hit event, both heritable and somatic. Taken together, these findings strongly suggest the involvement of a recessive oncogene linked closely to the polymerase gene on chromosome 13 and independent of Rb in the pathogenesis of several malignancies. Since this deletion on chromosome 13 affects a number of tumor types, it has been proposed to call this region M.E.S., for multiple etiological suppressor.

Having now fully described the invention, it will be understood that the same can be carried out within a broad and equivalent range of probes, conditions, enzymes, detection techniques, and the like without affecting the spirit or scope of the invention or any embodiment herein.

TABLE I

SUMMARY OF RFLP ANALYSIS
IN NORMAL POPULATION

| | |
|---|---|
| Total Cases | 94 |

TABLE I-continued
SUMMARY OF RFLP ANALYSIS IN NORMAL POPULATION

| 'A' Genotype | 80 |
|---|---|
| AB Genotype | 14 |
| B Genotype | 0 |

TABLE II
SUMMARY OF PADPR RFLP ANALYSIS IN BURKITT'S LYMPHOMA

|  | Polymorphic | | |
|---|---|---|---|
|  | 'B' Genotype | 'AB' Genotype | Normal |
| Sporadic | | | |
| EBV + | 1 | 0 | 7 |
| EBV − | 1 | 9 | 5 |
| Endemic | 8 | 11 | 1 |
| Not Known | 0 | 1 | 1 |

TOTAL CASES 45
AB GENOTYPES 20
B GENOTYPES 10

TABLE III
RFLP ANALYSIS IN B FOLLICULAR LYMPHOMAS

|  | Polymorphic | | |
|---|---|---|---|
|  | 'B' Genotype | 'AB' Genotype | Normal |
| Translocations | 4 | 7 | 8 |
| No Translocation | 0 | 0 | 4 |
| Non-Follicular | 0 | 0 | 1 |

TOTAL CASES 24
AB GENOTYPES 7
B GENOTYPES 4

TABLE IV
LUNG TUMORS

|  | Polymorphic | | |
|---|---|---|---|
|  | 'B' Haplotype | 'AB' Haplotype | Normal |
| SCLC | | | |
| LMYC Amplification | 2 | 4 | 0 |
| N/C MYC Amplification | 1 | 0 | 5 |
| No Amplification | 0 | 3 | 5 |
| NON SCLC | 1 | 2 | 1 |

TOTAL CASES 24
AB HAPLOTYPES 9
B HAPLOTYPES 4

TABLE V
LUNG CANCER LINES

| Tumor | Cell Line | myc activation | Chromosome 13 markers RB | ADPRT |
|---|---|---|---|---|
| 1. SCLC | 207 | L-myc | − | + |
| 2. SCLC | 187 | N-myc | + | − |
| 3. SCLC | 82 | c-myc | − | − |
| 4. SCLC | 417 | c-myc | − | − |
| 5. SCLC | 128 | L-myc | − | + |
| 6. SCLC | 69 |  | − | − |
| 7. SCLC | 378 | L-myc | + | + |
| 8. SCLC | 510 | L-myc | − | + |
| 9. SCLC | 345 | L-myc | + | + |
| 10. SCLC | 592 | N-myc | − | − |
| 11. non-SCLC | 787 |  | ND | + |
| 12. non-SCLC | 788 |  | ND | + |
| 13. non-SCLC | 789 |  | ND | + |
| 14. non-SCLC | 790 |  | ND | − |

SCLC = Small Cell Lung Carcinoma
+ = DNA somatic alteration
ND = not determined

TABLE VI
RFLP ANALYSIS IN BREAST TUMORS

|  | Polymorphic |
|---|---|
| A Genotype | 19 |
| B Genotype | 2 |
| Normal | 32 |
| TOTAL | 55 |

What is claimed is:

1. A method for detecting a DNA polymorphism associated with predisposition for cancer in a human, wherein said cancer is selected from the group consisting of Burkitt's lymphoma, B follicular cell lymphoma, acute myeloid leukemia, chronic myeloid leukemia, small cell lung carcinoma, and breast adenocarcinoma, comprising the steps of:
   (a) obtaining a biological sample having nucleated cells from a human;
   (b) isolating said nucleated cells from said biological sample;
   (c) isolating DNA from said nucleated cells;
   (d) digesting said DNA with the restriction enzyme HindIII to obtain DNA fragments;
   (e) separating fragments obtained from said digestion according to their respective molecular weights to form a pattern for said fragments;
   (f) detecting a DNA polymorphism associated with predisposition for cancer in a human with a hybridization probe which will hybridize to the gene for human poly(ADP-ribose) polymerase wherein said probe will also hybridize to at least one DNA fragment of about 2.5 to about 2.7 kilobases in a human with a predisposition for cancer.

2. A method for detecting a DNA polymorphism associated with predisposition for cancer in a human, wherein said cancer is selected from the group consisting of Burkitt's lymphoma, B follicular cell lymphoma, acute myeloid leukemia, chronic myeloid leukemia, small cell lung carcinoma, and breast adenocarcinoma, comprising the steps of:
   (a) obtaining a biological sample having nucleated cells from a human;
   (b) isolating said nucleated cells from said biological sample;
   (c) isolating DNA from said nucleated cells;
   (d) digesting said DNA with the restriction enzyme PstI to obtain DNA fragments;
   (e) separating fragments obtained from said digestion according to their respective molecular weights to form a pattern for said fragments;
   (f) detecting a DNA polymorphism associated with predisposition for cancer in a human with a hybridization probe which will hybridize to the gene for human poly(ADP-ribose) polymerase wherein said probe will also hybridize to a DNA fragment of about 5.7 kilobases to about 6.1 kilobases in a human with a predisposition for cancer.

3. A method for detecting a DNA polymorphism associated with predisposition for cancer in a human, wherein said cancer is selected from the group consisting of Burkitt's lymphoma, B follicular cell lymphoma, acute myeloid leukemia, chronic myeloid leukemia, small cell lung carcinoma, and breast adenocarcinoma, comprising the steps of:
   (a) obtaining a biological sample having nucleated cells from a human;

(b) isolating said nucleated cells from said biological sample;
(c) isolating DNA from said nucleated cells;
(d) digesting said DNA with the restriction enzyme EcoR1 to obtain DNA fragments;
(e) separating fragments obtained from said digestion according to their respective molecular weights to form a pattern for said fragments;
(f) detecting a DNA polymorphism associated with predisposition for cancer in a human with a hybridization probe which will hybridize to the gene for human poly (ADP-ribose) polymerase wherein said probe will also hybridize to a DNA fragment of about 5.1 kilobases in a human with a predisposition for cancer.

4. The method of any of claims 1 to 3 wherein said probe is cDNA for human poly (ADP-ribose) polymerase.

5. The method of any of claims 1 to 8 wherein said biological sample is selected from the group consisting of blood, tissue and sperm.

6. The method of any of claims 1 to 3 wherein said probe is detectably labelled.

7. A method for detecting susceptibility for cancer in a human, wherein said cancer is selected from the group consisting of Burkitt's lymphoma, B follicular cell lymphoma, acute myeloid leukemia, chronic myeloid leukemia, small cell lung carcinoma, and breast adenocarcinoma, comprising the steps of:
identifying the presence of a DNA polymorphism on chromosome 13 associated with susceptibility for cancer using a hybridisation probe which will hybridize to the gene for human poly (ADP-ribose) polymerase or closely linked sequences on chromosome 13 wherein the probe is capable of identifying said DNA polymorphism.

8. The method of claim 7 wherein said polymorphism is a restriction fragment length polymorphism (RFLP).

9. The method of claim 7 wherein said analyzing is comprised of the steps of:
(a) obtaining a biological sample having nucleated cells from a human;
(b) isolating said nucleated cells from said biological sample;
(c) isolating DNA from said nucleated cells;
(d) digesting said DNA with a restriction enzyme is selected from the group consisting of HindIII, Pst1, and EcoR1 to obtain DNA fragments;
(e) separating fragments obtained from said digestion according to their respective molecular weights to form a pattern for said fragments;
(f) detecting a DNA polymorphism associated with predisposition for cancer in a human with a hybridization probe which will hybridize to the gene for human poly (ADP-ribose) polymerase wherein said probe will also hybridize to a DNA fragment of a predetermined size in a human with a predisposition for cancer.

10. The method of claim 9 wherein said restriction enzyme is HindIII and said DNA fragment from about 2.5 to about 2.7 kilobases.

11. The method of claim 9 wherein said restriction enzyme is Pst1 and said DNA fragment from about 5.7 to about 6.1 kilobases.

12. The method of claim 9 wherein said restriction enzyme is EcoR1 and said DNA fragment about 5.1 kilobases.

13. The method of claim 9 wherein said probe is detectably labelled.

14. The method of claim 9 wherein said probe is CDNA for human poly (ADP-ribose) polymerase.

15. The method of claim 9 wherein said separating is by gel electrophoresis.

16. A restriction fragment length polymorphic probe comprising nucleic acid sequences which will hybridize to the gene for poly (ADP-ribose) polymerase and will also detect a DNA polymorphism associated with a susceptibility for cancer on human chromosome 13.

17. The probe of claim 16 wherein said nucleic acid sequences may be selected from the group consisting of genomic DNA, cDNA and mRNA.

18. The probe of claim 16 wherein said probe hybridizes to the gene or sequence adjacent to said gene for poly (ADP-ribose) polymerase on human chromosome 13.

19. The probe of any of claims 16, 17 or 18 wherein said probe hybridizes to a portion or fragment of said gene.

20. A method of monitoring cancer therapy comprising:
(a) detecting a polymorphism according to the method of claim 9;
(b) providing cancer therapy to the human from whom said nucleated cells were obtained; and
(c) detecting any changes in said polymorphism according to step (a).

* * * * *